United States Patent [19]

Doss

[11] 4,381,007
[45] Apr. 26, 1983

[54] MULTIPOLAR CORNEAL-SHAPING ELECTRODE WITH FLEXIBLE REMOVABLE SKIRT

[75] Inventor: James D. Doss, Los Alamos, N. Mex.

[73] Assignee: The United States of America as represented by the United States Department of Energy, Washington, D.C.

[21] Appl. No.: 258,970

[22] Filed: Apr. 30, 1981

[51] Int. Cl.$^3$ .............................................. A61B 17/36
[52] U.S. Cl. .............................. 128/303.1; 128/303.13
[58] Field of Search ........... 128/303.1, 303.13, 303.17, 128/303.18, 303.19, 804, 783, 422, 303.14

[56] References Cited

U.S. PATENT DOCUMENTS

| | | | |
|---|---|---|---|
| 1,951,731 | 3/1934 | Kassner | 128/804 |
| 3,078,850 | 2/1963 | Schein et al. | 128/303.13 |
| 3,307,553 | 3/1967 | Leibner | 128/400 |
| 3,978,864 | 9/1976 | Smith | 128/404 |
| 4,003,383 | 1/1977 | Brück | 128/404 |
| 4,202,337 | 5/1980 | Hren et al. | 128/303.14 |
| 4,326,529 | 4/1982 | Doss et al. | 128/303.1 |

FOREIGN PATENT DOCUMENTS 11844 of 1886 United Kingdom ................ 128/783

OTHER PUBLICATIONS

"A Technique for the Selective Heating of Corneal Stroma", Doss et al., Contact & Intraocular Lens Medical Jrl., vol. 6, No. 1, pp. 13-17, Jan-Mar., 1980.
"Shrinkage Temperature of Eye Collagen", Stringer et al., Nature, No. 4965, p. 1307, 1964.
"Thermokeratoplasty (TKP) Temperature Profile", Shaw et al., J. Invest. Ophthalmology, vol. 13, No. 3, pp. 181-186, 1974.
"Alterations in Corneal Morphology Following Thermokeratoplasty", Aquavell et al., Arch. Opthalmol., vol. 94, pp. 2082-2085, 1976.
"Thermokeratoplasty for Keratoconus", Keates et al., Opthalmol. Surg., vol. 6, No. 3, pp. 89-92, 1975.
"Thermokeratoplasty in the Treatment of Keratoconus", Gasset et al., Amer. Journal Opthalmol., vol. 79, No. 2, pp. 226-232, 1975.
A Technique for the Selective Heating of Corneal Stroma, Doss et al., Los Alamos Scientific Laboratory at the Univ. of Calif., Los Alamos, New Mexico, 87544, U.S. Dept. of Energy Contract W7405-Eng 36, 1978, LA-UR78-452.
An Electrochemical Technique for the Alteration of Corneal Curvature, Doss et al., Los Alamos Scientific Laboratory of Univ. of Calif., Los Alamos, New Mexico, 87544, U.S. Dept. of Energy Contract W-7405-Eng 36, LA 7155-MS.
'Los Alamos Keratoplasty Techniques', Rowsey et al., Contact and Intraocular Lens Medical Journal, vol. 6, No. 1, pp. 1-12, Jan-Mar., 1980.

*Primary Examiner*—Richard J. Apley
*Assistant Examiner*—J. L. Kruter
*Attorney, Agent, or Firm*—Robert W. Weig; Paul D. Gaetjens; Richard G. Besha

[57] ABSTRACT

The disclosure relates to a multipolar probe using radio-frequency energy to reshape the cornea of an eye. The surface of the cornea is flushed continuously with a conductive coolant during operation.

20 Claims, 13 Drawing Figures

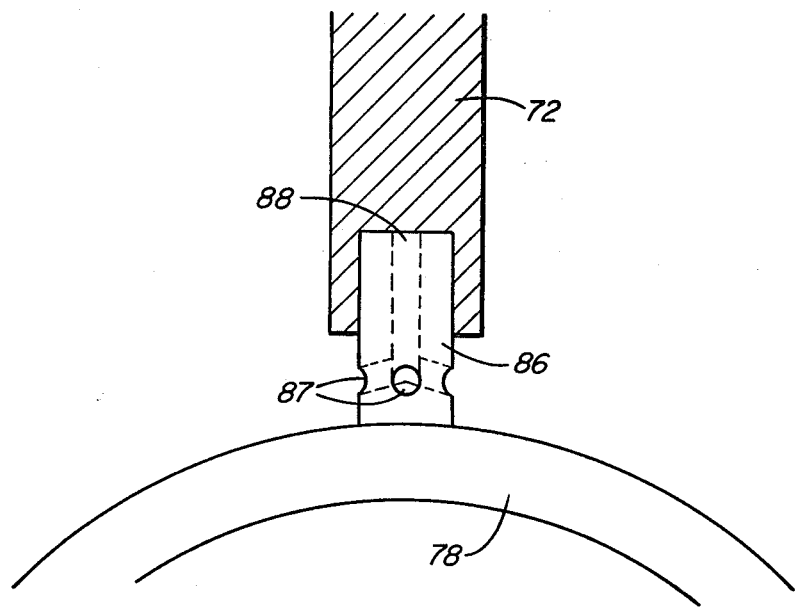
Fig. 10
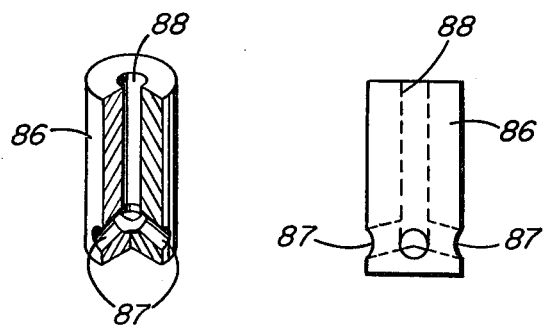
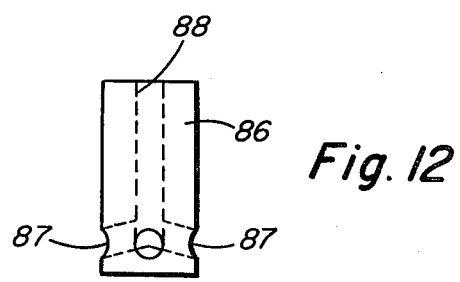
Fig. 12
Fig. 11
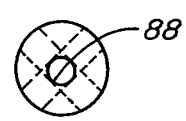
Fig. 13

MULTIPOLAR CORNEAL-SHAPING ELECTRODE WITH FLEXIBLE REMOVABLE SKIRT

This invention is the result of a contract with the Department of Energy (Contract No. W-7405-ENG-36).

BACKGROUND OF THE INVENTION

The invention relates to corneal reshaping and more particularly to multipolar electrodes utilizing radio-frequency electrical current to heat and thereby induce reshaping of the cornea in mammals.

Extreme cases of refractive error, such as those caused by keratoconus, are frequently not correctable by the addition of external refraction. Corneal transplant is the usual remedy. Recent alternatives have been suggested which include modification of the corneal shape by thermal methods which rely upon dramatic shrinkage of corneal collagen in about 55° to 65° Centigrade (C.) range. The use of these thermal methods has been limited by damage to the epithelium and Bowman's membrane, and by the temporary nature of the change affected. Each of these problems appear to be related to the thermal dose profile within the cornea which is generated by conventional conductive heating apparatus. Temperatures reached in the epithelium are relatively high while temperatures reached in the deeper stromal collagen are below the critical shrinkage temperature needed. A wide variability in treatment results exists which is probably caused by unintentional variation in individual techniques in administering thermal treatments, particularly in the length of time that heat is applied.

A corneal shaping electrode is disclosed in U.S. Pat. No. 4,326,529 issued Apr. 27, 1982 by James D. Doss and Richard L. Hutson, and is also described in "A Technique for the Selective Heating of Corneal Stroma," Contact and Intraocular Lens Medical Jrl. 6, No. 1, pp. 13–17 (January–March 1980). The monopolar electrode therein has been utilized on several mammals satisfactorily. The instant invention improves upon the monpolar electrode disclosed in U.S. Pat. No. 4,326,529. For example, no remote electrode is utilized. This means a patient's hair and skin at the rear of his head need not be wetted and cleansed because no remote electrode need be applied thereto. Too, because there is no remote electrode attached to the rear of the head, much less current need flow through the patient's brain and optic nerve. In addition, inherently high electric fields at the edge of the treatment region of the corneal shaping electrode of U.S. Pat. No. 4,326,529 are avoided by utilizing the present invention. Further, in practicing the instant invention, high current density and high coolant velocity are disposed in the same location on the corneal surface, providing highly effective removal of superficial heat.

In the monopolar probe of U.S. Pat. No. 4,326,529 electric current flows away from the probe in a direction that is approximately perpendicular to the surface of the cornea. In the present invention, current flows substantially parallel to the corneal surface between at least two electrode tips although there is a significant perpendicular component electric current immediately under a metallic electrode.

SUMMARY OF THE INVENTION

One object of the present invention is to provide correction of complex corneal refractive errors virtually impossible to correct with external refraction.

Another object of the present invention is to provide corrections to corneas without conventional surgery.

Another object of the present invention is to provide correction of common corneal refractive errors and thus eliminate the need for external correction.

One advantage of the invention is that superficial corneal tissue is effectively cooled and thereby protected while allowing deeper corneal tissue to be heated sufficiently to correct refractive errors therein.

Another advantage of the instant invention is that the temperature increases effected within the cornea are sufficiently deep that they enter collagen fibers, resulting in permanent changes in corneal shape.

Another advantage of the instant invention is that corneal reshaping can be achieved without the use of a remote electrode.

Yet another advantage of the instant invention is that very little current need pass through a patient's brain and optic nerve.

Still another advantage is that there are no high electic fields at the edge of the area of treatment.

Another advantage of the instant invention is that high current densities and high coolant flow velocity are inherently in the same region on the corneal surface, thereby effectively protecting all of the superficial layers of corneal tissue.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

In accordance with the present invention there is provided an apparatus utilizing radio-frequency energy for corneal reshaping comprising a source of alternating voltage, a plurality of tubular electrodes having tips operably connected to the source of alternating voltage, a housing disposed about the plurality of electrodes and an electric insulation incorporated between the electrodes. The tips of the electrodes are positionable adjacent and spaced from a subject cornea. A liquid electrically conductive coolant is made to flow through or adjacent to at least one of the electrodes onto the cornea, then, from the cornea, through or adjacent to the other electrode. A damming device such as a flexible skirt retains the coolant over the cornea so that it does not run off. The electrodes can be spaced adjacent electrodes in which case the tips are preferably substantially oval or rectangular in cross section. In such a case the insulation may comprise partitioning between the electrodes, the partitioning having one or more apertures for coolant flow thereunder. The aperture can be arcuate or "comb" shaped, the latter providing distance retention between the cornea and the metallic electrode tips. The electrodes may be two, three or more, substantially parallel and spaced. The electrodes may also be concentric or coaxial and a fluid conducting spacer used to retain electrode to cornea spacing.

BRIEF DESCRIPTION OF THE DRAWINGS

The accompanying drawings, which are incorporated in and form a part of the specification, illustrate several embodiments of the present invention and, together with the description, serve to explain the principles of the invention. In the drawings:

FIG. 10 illustrates a spacer which may be utilized in the embodiment shown in FIG. 7; and FIGS. 11, 12, and 13 show various views of the spacer of FIG. 10.

DETAILED DESCRIPTION OF THE INVENTION

Figure 9:
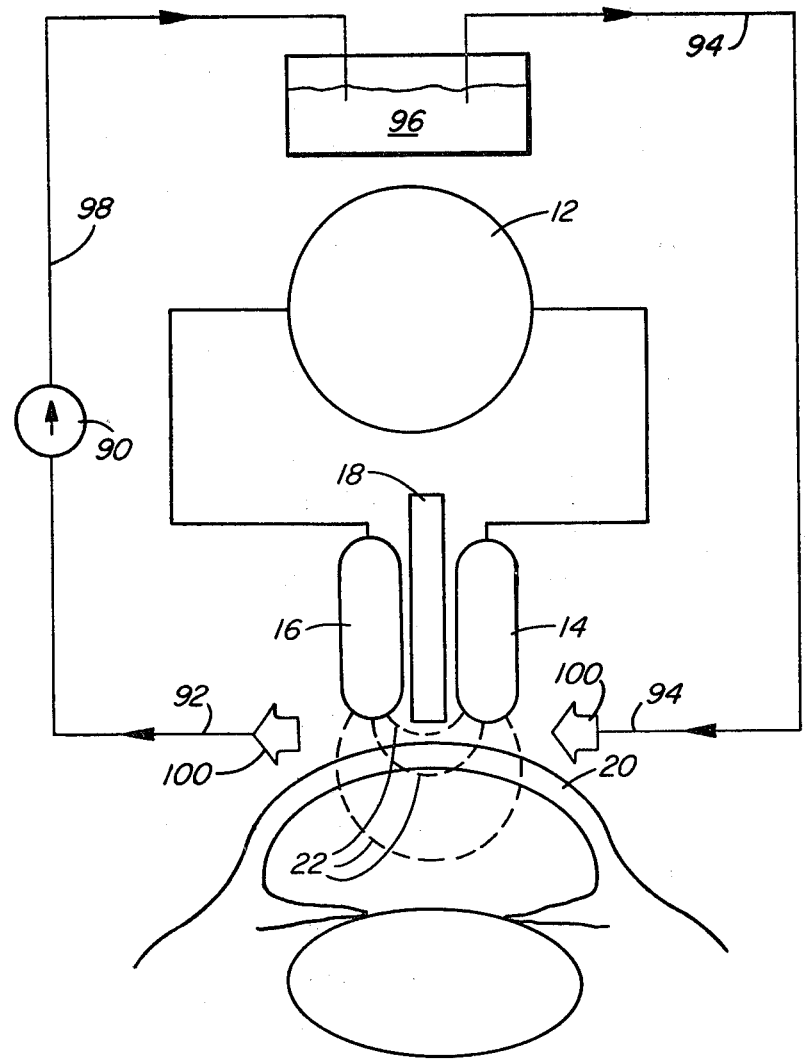
FIG. 9 schematically illustrates the present invention.

Reference is made to FIG. 9 which schematically shows a two-electrode embodiment of the invention. A source of alternating voltage 12 such as a radio-frequency generator producing a 0.1 to 20 megahertz electric current is operably connected to electrodes 14 and 16. It will be appreciated by those skilled in the art that any radio-frequency current between about 100 kHz and about 20 mHz producing between about 20 and 200 $V_{rms}$ for a duration of from about 1 to about 10 seconds is suitable. It will also be appreciated by those skilled in the art that different voltage and current levels and different electrode dimensions may be utilized for heating different corneal areas and depths and that current density generally decreases as a function of corneal depth. Decrease in current density is essentially a function of electrode configuration. In general, larger electrodes cause deeper heating. Separating electrodes 14 and 16 is an electrically insulating partition 18. The electrodes including the insulating partition are positionable over the surface of a cornea 20. During operation, an electrically conductive coolant solution may be pumped by a pump 90 from a tank 96 through a conduit 94, over the surface of the cornea 20, under the tips of the electrodes 14 and 16 and insulating partition 18 and back to tank 96 through conduit 92, pump 90 and conduit 98. Direction of coolant flow is further shown by arrows 100. Dotted lines 22 show the radio-frequency electric field produced by electrodes 14 and 16. A device to retain the flow over the cornea is not shown in FIG. 9, but may be seen for example in FIG. 1 where input tubular conduit 94 is shown attached to an electrode 34, and output tubular conduit 92 is shown connected to an electrode 36. Tubular conduits 92, 94 and 98 may, for example, comprise flexible, electrically insulated tubing such as Neoprene tubing commonly used for liquid flow.

The conductive coolant solution preferably comprises isotonic saline but may be hypotonic or hypertonic to alter the electrical resistivity of the saline when desired. Importantly, the saline solution provides electrical conduction to the corneal surface for the radio-frequency current and acts as a coolant for layers of the cornea near the surface thereby providing protection of superficial tissue during the heating of deeper corneal tissues which are the tissues needed to be heated in order to effect relatively permanent changes in corneal shape.

A problem unsolved by prior art thermokeratophores is that the thermal energy deposited in the epithelium is greater than that in the deeper stroma. Ser. No. 100,664 teaches that some epithelia heat must be removed if that portion of the cornea is not to be overheated. The problem is solved in U.S. Pat. No. 4,326,529 and in the instant invention using electrically conductive coolant.

Figure 1:
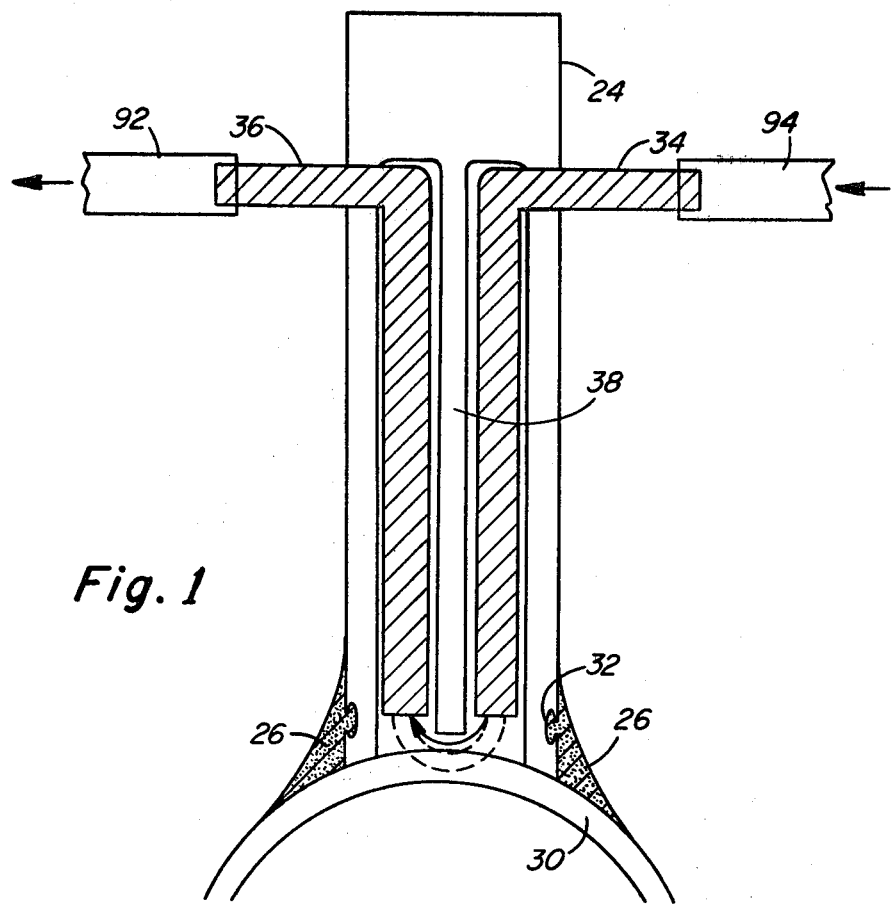
FIG. 1 illustrates a preferred embodiment of the invention.
Figure 2:
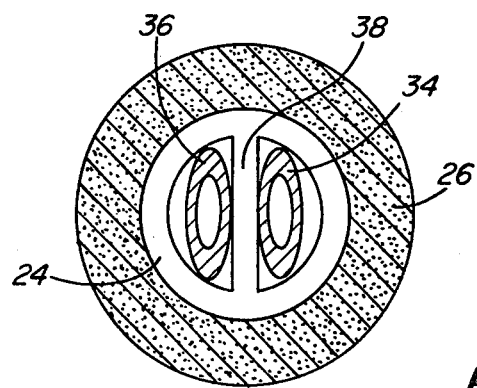
FIG. 2 is an end view of the device of FIG. 1.
Figure 3:
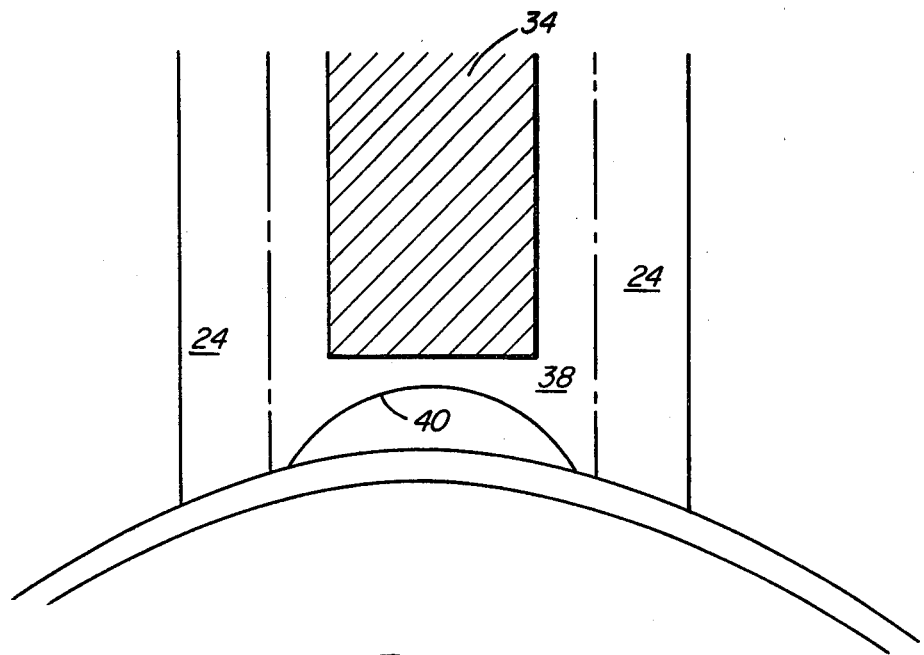
FIGS. 3 and 4 show insulating partitions suitable for use in the preferred embodiment of FIGS. 1 and 2 as well as the embodiment of FIGS. 5 and 6.
Figure 4:
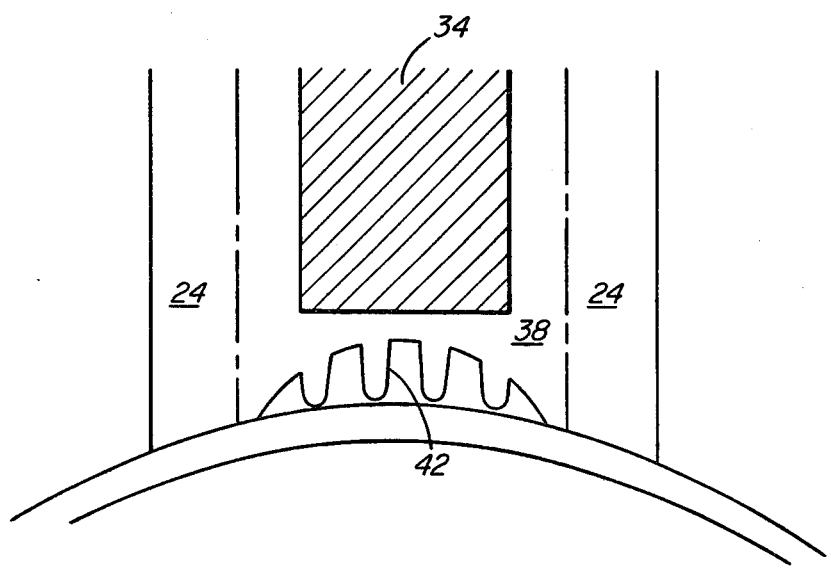

Reference is now made to FIG. 1 which shows a housing 24 which may comprise, for example, a non-conductive plastic. The housing is preferably generally cylindrical in shape so that a user's hand may comfortably hold it over an eye. Attached circumferentially about the base of the housing is a flexible skirt 26 which acts as a damming device for the coolant. Skirt 26 preferably generally conforms to the surface of a cornea 30. As seen in FIG. 1, a notch or groove 32 may be provided in housing 24 as an attachment means for skirt 26 which may have a ridge thereon fittable within the groove. Thus, the skirt may be readily changed to effectuate easy sterilization, change of skirt size and the like. Tubular electrodes 34 and 36 are contained within the housing 24 and are connected to the recirculating pump 90 and reservoir 96 seen in FIG. 9 through flexible tubular lines 92 and 94, respectively. Coolant enters the device through tubular electrode 34, flows over the surface of cornea 30, and exits through tubular electrode 36. An insulating partition 38 is disposed between electrodes 34 and 36 which, in this embodiment, are essentially parallel and spaced from one another. It will be noted that the tip of insulator 38 does not touch the surface of the cornea so that saline may flow from one electrode over the surface of the cornea and into the other electrode. Alternatively, the partition ends seen in FIGS. 3 and 4 may be used. FIG. 3 shows an arcuate aperture having edge 40. FIG. 4 illustrates a "comb" aperture having edge 42. The FIG. 4 comb retains the cornea at a fixed distance from the tips of the electrodes. This is quite useful since the cornea tends to be drawn into the aperture if a vacuum is used to cause coolant flow. FIG. 2 is an end view of the embodiment of FIG. 1 showing the flexible skirt 26 surrounding housing 24 and insulator 38 between electrodes 36 and 34. As can be seen therein, the tips of the electrodes are substantially oval in cross section. The bipolar corneal electrode of FIGS. 1 and 2 can be referred to as a double parallel tube type. The electrodes may comprise stainless steel and may be coated with gold to inhibit corrosion in the saline environment. The plastic housing 24 may be an acrylic or C.A.B. plastic. The skirt may typically comprise a silicone rubber material such as Dow Corning ® 3110 RTV. Other suitable materials for electrodes, housing, insulators, and the like will be apparent to those skilled in the art.

Figure 5:
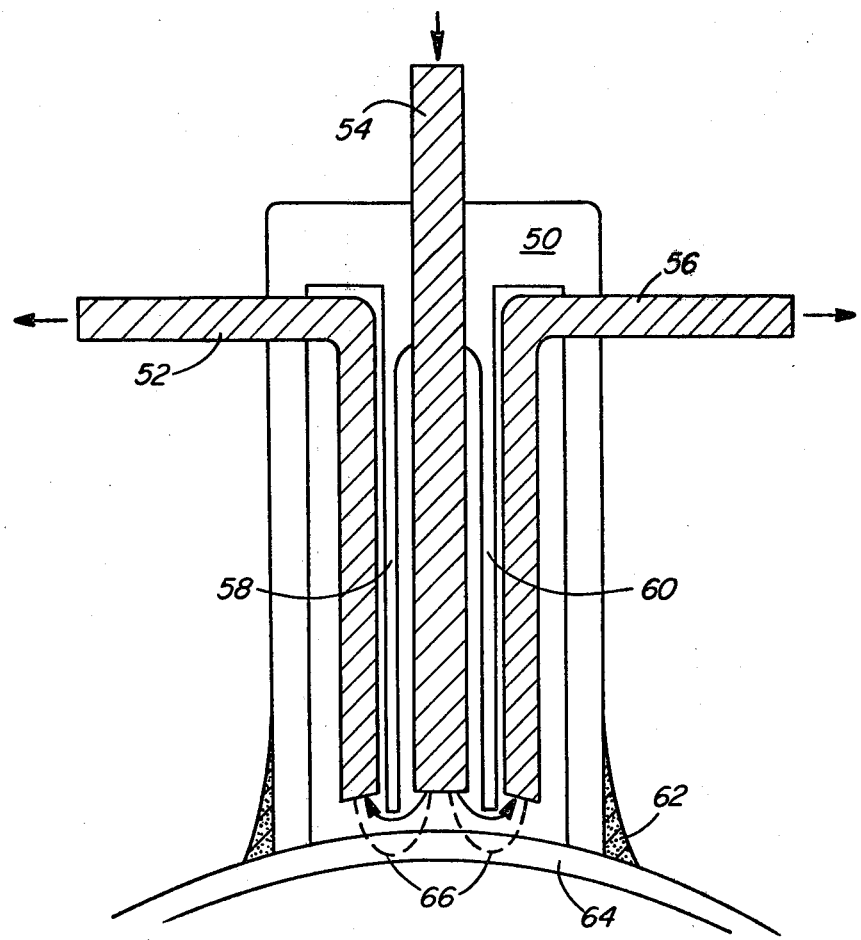
FIG. 5 illustrates a quardrapole embodiment of the invention.
Figure 6:
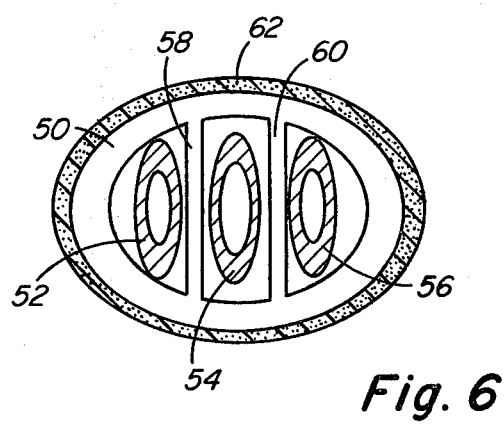
FIG. 6 depicts an end view of the FIG. 5 embodiment.

The insulating partition tips shown in FIGS. 3 and 4 may also be utilized in the embodiment of FIGS. 5 and 6. As shown therein, an insulative housing 50 which is generally cylindrical so that it may be readily held by a user's hand contains three electrodes 52, 54, and 56 which are separated by insulating partitions 58 and 60. For any multiple-electrode device such as the quardrapole example shown in FIGS. 5 and 6, adjacent electrodes would generally be connected to opposite terminals of the radio-frequency source. For example, electrodes 52 and 56 of FIG. 5 are connected together and connected to one terminal of a radio-frequency source. Center electrode 54 is connected to the opposite terminal of the radio-frequency source. A flexible skirt 62 is fixed about the base of housing 50 and may be attached thereto by ridge and groove as in the FIGS. 1 and 2 embodiment, by friction or otherwise. The base of the housing may rest on the surface of a cornea 64. In this embodiment of coolant is preferably introduced through central electrode 54, circulates under insulating partitions 58 and 60, and is removed from the surface of the cornea through lateral electrodes 52 and 56. Coolant may flow in the opposite direction, alternatively. Electric field lines 66 are as illustrated. As seen in FIG. 6, the housing 50 of this embodiment may be substantially oval in cross section as are the tips of the electrodes 52, 54, and 56. The advantage of the multipolar electrode of FIGS. 5 and 6, also known as a quadrapole because the center counts as two poles, are that larger corneal regions may be heated without unwanted heating at greater depths as could occur with only two (larger) electrodes. The device of this as well as the FIGS. 7 and 8 embodiment may comprise the same materials as the FIGS. 1 and 2 embodiment.

Figure 7:
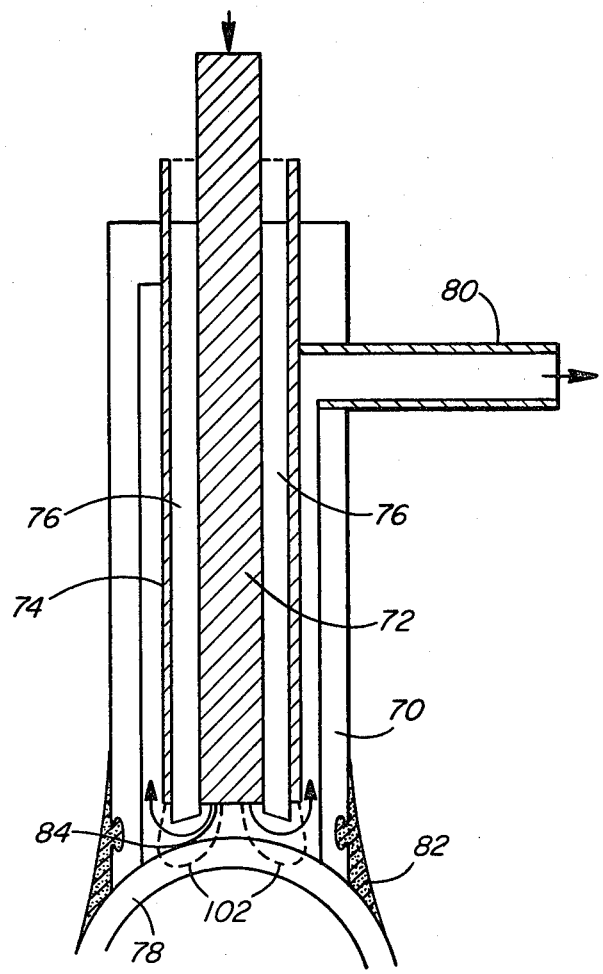
FIG. 7 illustrates a coaxial concentric electrode embodiment in accordance with the present invention.
Figure 8:
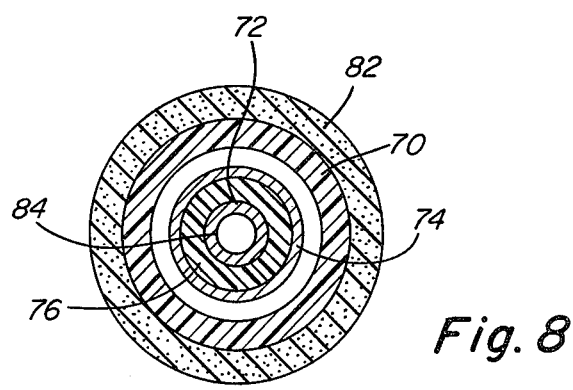
FIG. 8 shows an end view of the FIG. 7 embodiment.

FIGS. 7 and 8 illustrate a concentric bipolar electrode configuration comprising a housing 70 and concentric tublar electrodes 72 and 74 separated by a tubular insulating member 76, also concentric with the two electrodes. A flexible skirt 82 similar to those of the previously described embodiments is utilized. Coolant introduced through the central electrode 72 passes over the surface of cornea 78 through aperture 84 and exits between the housing 70 and the outer surface of outer electrode 74. Communicating with the tubular aperture between electrode 74 and housing 70 is a conduit 80 through which the coolant is drawn off. Electric field lines 102 illustrate the radio-frequency electric field introduced into the cornea by the electrodes of this embodiment. FIG. 8 illustrates end-on the flexible skirt 82, housing 70, outer electrode 74, tubular insulating member 76, and inner electrode 72. An advantage of this particular electrode configuration is that a ring or torus-shaped treatment region can be realized since electric current flows essentially in a torus-shaped volume under and between electrodes 72 and 74. Such a treatment volume leaves an untreated and relatively protected region in the central region of the torus, which may be used in practice to protect the region of cornea immediately over the pupil of the eye.

Referring now to FIG. 10, when a vacuum is used to causes the coolant to flow over the corneal surface, it may often be desirable to provide the probe shown in FIGS. 7 and 8 with an insulating spacer 86 seen in FIGS. 10–13 disposed at the tip of inner electrode 72. The spacer serves to keep the cornea 78 at an appropriate distance from electrodes 72 and 74 shown in FIG. 7 as the cornea tends to be pulled towards said electrodes by a vacuum pumped coolant. Details of a typical spacer 86 are illustrated in FIGS. 10–13. In FIG. 10, spacer 86 is shown resting on cornea surface 78 and attached to the inner surface of inner electrode 72 which is also shown in FIGS. 7 and 8. In the illustrative example shown in FIGS. 10–13, the spacer 86 is provided with an orifice 88 which communicates with multiple radial outlets 87 to provide coolant flow through the spacer and over the cornea.

In all three illustrated embodiments the flow velocity of the convective cooling agent, i.e., the saline solution, typically is highest at the region of the corneal surface where the electric field intensity is highest. This is very advantageous because it inherently protects the most important superficial tissues of the cornea.

A bipolar probe similar to the embodiment shown in FIGS. 1 and 2 with an insulator tip similar to the one illustrated in FIG. 3 was tested on several rabbit corneas. The only significant experimental difficulty was related to the fact that vaccum-driven coolant caused the cornea to move into the aperture, partially blocking coolant flow. This difficulty was later solved by the introduction of an aperture similar to the one shown in FIG. 4. Nevertheless, the experiments were successful. There were noticeable effects upon endothelial tissue, considered to be primarily due to extra mechanical stresses caused by the vacuum pulling the cornea partially into the aperture between the electrodes. Other probes, similar to the one shown in FIGS. 1 and 2 were built. An aperture of the "comb" type illustrated in FIG. 4 was made. In further tests, it was noted that performance of this embodiment of the instant invention was quite excellent. The excellent performance was apparently enhanced by the utilization of the "comb" type aperture shown in FIG. 4. This aperture, while allowing sufficient flow of coolant across the corneal surface, retains the cornea at a proper distance from the electrodes. The rabbit corneas treated in the second experiment did not exhibit the slight damage caused by mechanical stress on the endothelium which had been seen following the earlier experiment. This is probably explained by the action of the "comb" aperture retaining the cornea from being pulled towards the electrodes by the vacuum used to create coolant flow.

Those skilled in the art will appreciate that approximate electric field configurations can be calculated for the various embodiments illustrated in the drawings to determine which embodiment may be best suited for a particular type of corneal treatment.

The foregoing description of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus utilizing radio-frequency electrical energy without a remote electrode for reshaping a cornea comprising:
   a plurality of electrode means having tips;
   housing means disposed about said plurality of electrode means;
   insulating means disposed within said housing means between said electrode means;
   means for positioning said tips of said electrode means adjacent but spaced from a cornea to be reshaped;
   means for producing an alternative voltage in the radio-frequency range;

means for applying said radio-frequency voltage to said tips of said electrode means and thereby radio-frequency energy in a preselected pattern to the cornea to be reshaped;

means for flowing an electrically conductive liquid coolant in the vicinity of one said tip, over the cornea, and from the cornea in the vicinity of another tip; and flexible skirt means removably secured to said housing means for effectively damming said coolant over the cornea so that it does not run off.

2. The invention of claim 1 wherein said damming means comprises a skirt on said housing means.

3. The invention of claim 2 wherein said skirt is flexible.

4. The invention of claim 2 wherein said skirt is detachably affixed to said housing.

5. The invention of claim 1 wherein said housing comprises insulative material.

6. The invention of claim 1 wherein said tips of said electrode means are substantially oval in cross section.

7. The invention of claim 1 wherein said plurality of electrode means are substantially parallel.

8. The invention of claim 1 wherein said fluid flowing means comprises means for flowing said coolant through said electrode means.

9. The invention of claim 1 wherein said insulating means comprise partitions among said plurality of electrode means.

10. The invention of claim 9 wherein said positioning and insulating means comprise a partition extending beyond said electrode means tips to contact the cornea and properly space said electrode means tips therefrom, said partition providing a passageway for coolant flow across the surface of the cornea.

11. The invention of claim 10 wherein said partition comprises a comb passageway to maintain the cornea a preselected distance from said electrode means tips.

12. An apparatus utilizing radio-frequency energy to reshape a cornea comprising:

an alternating voltage source;

first, second, and third tubular electrodes, each having a tip, and each operably connected to said alternating voltage source;

insulating means disposed between said electrodes to insulate one from another;

a housing disposed about said electrodes and said insulating means;

means for positioning said electrode tips a selected distance from the surface of the cornea;

means for conducting an electrically conductive liquid coolant through at least one of said electrodes onto and over the cornea and then up at least one of the electrodes; and flexible skirt means removably secured to said housing for retaining said coolant over the cornea.

13. The invention of claim 12 wherein said coolant retaining means commprises a flexible skirt on said housing.

14. The invention of claim 12 wherein said tubular electrodes are essentially parallel.

15. The invention of claim 12 wherein said electrode tips are essentially oval in cross section.

16. The invention of claim 12 wherein said tubular electrodes are essentially parallel, comprising two end and one center electrode and spaced in a line, said coolant conducting means comprising means for conducting coolant through the center electrode onto the cornea and from the cornea through said two end electrodes.

17. An apparatus for reshaping a cornea using radio-frequency energy, said apparatus comprising:

a source of alternating voltage;

an inner tubular electrode having a tip and operably connected to said alternating voltage source;

an outer tubular electrode having a tip operably connected to said alternating voltage source and annularly disposed about and spaced from said first tubular electrode;

annular means for insulating said inner and outer electrodes from one another;

a housing disposed about said inner and outer electrodes and said insulating means;

means for positioning said inner and outer electrode tips a selected distance from the cornea;

means for conducting a liquid coolant onto the cornea and from the cornea; and flexible skirt means removably secured to said housing for containing the coolant over the cornea.

18. The invention of claim 17 wherein said coolant conducting means comprise means for flowing the coolant through said inner electrode over the cornea and from the cornea between said outer electrode and said housing.

19. The invention of claim 17 wherein said coolant containing means comprise a flexible skirt affixed to said housing.

20. The invention of claim 17 wherein said tips of said tubular electrodes are essentially circular in cross section.

* * * * *